United States Patent [19]

Sturtzkopf

[11] Patent Number: 4,573,916
[45] Date of Patent: Mar. 4, 1986

[54] DEVICE FOR DETERMINING THE RELATIVE POSITION OF THE UPPER JAW AND LOWER JAW FOR THE PRODUCTION OF DENTURES

[76] Inventor: Robert Sturtzkopf, Wilhelm-Hey-Str. 14, 8000 Munich 60, Fed. Rep. of Germany

[21] Appl. No.: 637,395

[22] Filed: Aug. 3, 1984

[30] Foreign Application Priority Data

Aug. 12, 1983 [DE] Fed. Rep. of Germany ....... 3329284

[51] Int. Cl.⁴ .............................................. A61C 9/00
[52] U.S. Cl. ..................................................... 433/71
[58] Field of Search ..................................... 433/71, 46

[56] References Cited

U.S. PATENT DOCUMENTS 2,773,308 12/1956 Van Court et al. ................... 433/71

4,445,856 5/1984 Sturtzkopf .

FOREIGN PATENT DOCUMENTS 3104721 1/1983 Fed. Rep. of Germany .

*Primary Examiner*—Robert Peshock
*Attorney, Agent, or Firm*—Harness, Dickey & Pierce

[57] ABSTRACT

A device for mutual alignment of the upper and lower jaw for the purpose of producing dentures utilizes a bag to be interposed between the upper and lower jaw and which bag is filled with a freely shapeable, hardening material which is allowed to harden once the jaws have been firmly closed on each other. The bag has a recess in the region of the frontal teeth. The filling opening is provided with a valve allowing an easy filling, but preventing the material from being squeezed out when the patient is biting. Perforations are provided to facilitate a bubble free filling of the material.

4 Claims, 3 Drawing Figures

4,573,916

DEVICE FOR DETERMINING THE RELATIVE POSITION OF THE UPPER JAW AND LOWER JAW FOR THE PRODUCTION OF DENTURES

BACKGROUND OF THE INVENTION

U.S. Pat. No. 4,445,856 refers to a method and device for mutual alignment of the chewing surfaces of the upper jaw and the lower jaw for the purpose of producing dentures.

For this a fork-like bag made of plastic material is utilized which is preferably filled with creamy gypsum and which is then interposed between the teeth or, respectively, between provisional prostheses made of wax. The patient bites on the liquid wadding with a moderate force with the wadding being filled to an extent to just prevent a mutual contact of the teeth. The teeth rather float with respect to each other, but do not mutually engage. As long as the gypsum is still liquid, the patient has the possibility to laterally move the lower jaw in a testing manner to find out on a most convenient position of the lower jaw in which exerting biting force is sensed to meet the smallest resistance. Once this particular position is found the patient keeps it until the gypsum hardens. The shape of the hardened bag accurately corresponds to the physiologically proper mutual alignment of the chewing surfaces of the upper and lower jaw.

The method of the patent referred to avoids substantial disadvantages of other known registering methods. This particularly applies to methods which utilize one or more supporting pins provided at the provisional prosthesis for registering the position between the upper and lower jaw. Such method is complicated. Furthermore, a correction of the position of the lower jaw after brought into contact with the upper jaw cannot be obtained free of interference, since a free interplay of the jaws to find the proper alignment is not possible. In utilizing a wax impression, where the patient bites on a piece of wax which after warming is interposed between the teeth, any correction in position of the lower jaw with respect to the upper jaw is not possible since the wax obstructs a free sliding motion.

SUMMARY OF THE INVENTION

It is an object of the present invention to improve the device according to the patent above referred to under the aspect of increasing the precision of the impression, to improve the precision of the proper alignment between the upper and lower jaw prosthesis and finally to facilitate the handling of the plastic bag.

The approvements achieved by the present invention are obtained by a device for determing the mutual alignment of the chewing surfaces of the upper and lower jaw for the purpose of producing dentures, wherein a freely shapeable wadding is interposed between the upper and lower jaw which is allowed to harden once the chewing surfaces have been firmly closed on each other, and wherein the wadding comprises a plastic bag in a fork-like shape including a filling opening which is elongated in a tubular shape at the center as an elongation of the shanks, said bag further including a recess in the area of the frontal teeth and tubular connections for connecting the shanks outside the area of the frontal teeth to each other and to the filling opening.

It is of particularly advantage to provide the bag with a recess in the region of the frontal teeth, in particular the incisors, to prevent impressions of said teeth. This avoids an interference caused by a liquid wadding located between the frontal teeth which could be an obstruction to impede the spacial alignment of upper and lower jaw.

According to the invention a valve is provided for the filling opening of the bag to facilitate the filling and to avoid that in firmly closing the jaws on each other filling material is squeezed out from the bag.

According to the invention the shanks of the bag are further provided with perforations to ensure that the bag is completely filled allowing air to flow out through the perforations which air could otherwise cause air bubbles in the bag.

BRIEF DESCRIPTION OF THE DRAWING

An embodiment of the invention is described below with reference to the accompanying drawing in which.

DETAILED DESCRIPTION OF THE PREFERRED EMBODIMENT

Figure 1:
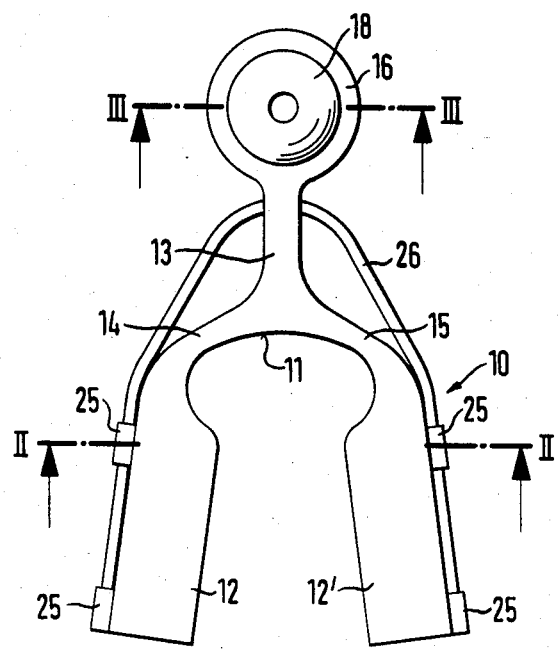
FIG. 1 shows a top view of the bag including a holder.
Figure 2:
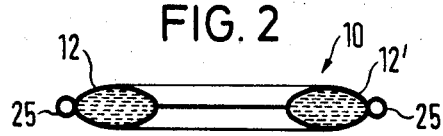
FIG. 2 is a sectional view of the bag taken along the line II—II of FIG. 1.
Figure 3:
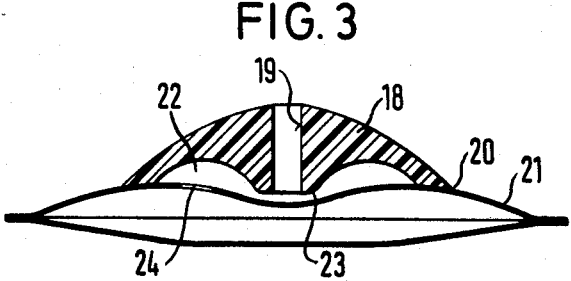
FIG. 3 is a sectional view taken along the line III—III of FIG. 1 in a larger scale.

In the drawing a bag 10 is shown which is made of a pair of thin plastic foils which are connected along their margins by welding. In the area of the frontal teeth the bag 10 has a recess defined by the line 11. Both shanks 12 and 12' are utilized to make impressions of the molars. A frontal elongation 13 of tubular shape through which a hardening material, for example gypsum is filled into the bag 10, is connected through a tubular extension 14 and 15 each with the shanks 12 and 12'. The end of the prolongation 10 is broadened as shown at 16 to provide a supporting face for a valve cap 18 which is shown in cross section in FIG. 3.

The valve cap 18 comprises a central filling opening 19 to receive a syringe filled with stirred gypsum. The edge 20 of the cap 18 is sealingly connected to the adjacent wall 21 of the bag by welding for example. The cap 18 further provides for a circular hollow space 22 above the foil 21 which space is isolated with respect to the passage 19 by a circular web portion 23. A filling hole 24 in the bag opens into the hollow space 22.

When the gypsum is urged through the filling passage 19, the wall 21 is moved away from the web 23 and the gypsum may enter the hollow space 22 and from their through the hole 24 into the bag. However, when pressure is exerted on the bag by the biting of the patient, the wall 21 is urged towards the web 23 thus preventing the back flow of material from the space 22 to the passage 19. In this manner the cap 18 in relation with the wall 21 and the filling hole 24 which is laterally displaced with respect to the passage 19 define a check valve.

To ensure a bubble free filing of the bag 10, the shanks 12 and 12' of the bag are provided with very fine perforations. While the gypsum is being filled in, any air may escape through the perforations, but not the gypsum such that the bag is filled free of air bubbles.

After filling the bag the patient is allowed to bite on the bag. The teeth of the provisional prosthesis become no contact to each other, but rather float above each other, enabling the patient by lateral motions of the chaws to find the proper mutual alignment of the upper and lower jaw by a test and trial method. In this position the patient must wait until the gypsum has hardened within the about 30 to 60 seconds. Thereafter the mutual position of the upper and lower jaw prosthesis is exactly determined, whereupon the bag may be removed from the hardened gypsum.

Along both outer margins of the bag projections 25 are provided to receive a wire handle 26.

What is claimed is:

1. A device for determining the mutual alignment of the chewing surfaces of the upper and lower jaw for the purpose of producing dentures, wherein a freely shapeable hardenable wadding is interposed between the upper and lower jaw which is allowed to harden once the chewing surfaces have been firmly closed on each other and wherein the wadding comprises a plastic bag in fork-like shape having a pair of shanks each adapted to be engaged by the molars at the respective sides of the mouth of a user, including a filling opening which is elongated in a tubular shape and communicating with the interior of the shanks, the improvement comprising said bag being recessed in the area of the frontal teeth sufficiently not to be engaged thereby when said shanks are engaged by the molars and providing tubular connections for connecting the shanks of the bag outside the area of the frontal teeth to each other and to the filling opening.

2. The device of claim 1, wherein the filling opening comprises a check valve.

3. The device of claim 2, wherein the valve comprises a cap secured to an enlarged portion of the central elongation, said cap comprising a central filling passage, a hollow space laterally displaced with respect to the filling passage and a circular projection for cooperating with the adjacent wall of the bag, said filling opening of the bag opening into the hollow space.

4. The device of claim 1, wherein the wall of the shank portions is perforated.

* * * * *